United States Patent
Sroufe et al.

(10) Patent No.: US 6,554,785 B1
(45) Date of Patent: Apr. 29, 2003

(54) THERAPEUTIC COMBINATION GEL AND AIR BLADDER PACK

(76) Inventors: Jon W. Sroufe, P.O. Box 347, Ligonier, IN (US) 46767; James E. Sroufe, P.O. Box 347, Ligonier, IN (US) 46767; Jeffrey S. Wells, P.O. Box 347, Ligonier, IN (US) 46767

( * ) Notice: Subject to any disclaimer, the term of this patent is extended or adjusted under 35 U.S.C. 154(b) by 0 days.

(21) Appl. No.: 09/977,077

(22) Filed: Oct. 12, 2001

Related U.S. Application Data

(60) Provisional application No. 60/240,266, filed on Oct. 13, 2000.

(51) Int. Cl.[7] .............................. A61F 5/00; A61F 5/37
(52) U.S. Cl. ............................ 602/23; 128/882; 602/27
(58) Field of Search ................... 602/13, 5, 19, 602/16, 27, 23; 601/71

(56) References Cited

U.S. PATENT DOCUMENTS

| | | |
|---|---|---|
| 3,548,420 A | 12/1970 | Spence |
| 3,780,537 A | 12/1973 | Spencer |
| 3,885,403 A | 5/1975 | Spencer |
| 3,901,225 A | 8/1975 | Sconce |
| 4,243,041 A | 1/1981 | Paul |
| 4,280,489 A | 7/1981 | Johnson |
| 4,495,942 A | 1/1985 | Palumbo |
| 4,502,470 A | 3/1985 | Kiser |
| 4,572,169 A | 2/1986 | Mauldin |
| 4,590,932 A | 5/1986 | Wilkerson |
| 4,628,945 A | 12/1986 | Johnson |
| 4,671,267 A | 6/1987 | Stout |
| 4,844,094 A | 7/1989 | Grim |
| 4,869,267 A | 9/1989 | Grim |
| 4,905,998 A | 3/1990 | Last |
| 4,953,543 A | 9/1990 | Grim |
| 4,964,402 A | 10/1990 | Grim |
| 4,993,409 A | 2/1991 | Grim |
| 5,026,339 A | 6/1991 | Kasper |
| 5,027,801 A | 7/1991 | Grim |
| 5,062,414 A | 11/1991 | Grim |
| 5,088,478 A | 2/1992 | Grim |
| 5,125,400 A | 6/1992 | Johnson |
| 5,205,814 A * | 4/1993 | Lundrigan et al. ... 128/DIG. 20 |
| RE34,661 E | 7/1994 | Grim |
| 5,366,439 A * | 11/1994 | Peters .................... 602/13 |
| RE35,113 E | 12/1995 | Grim |
| 5,716,335 A * | 2/1998 | Iglesias et al. ............. 602/16 |
| 5,951,504 A * | 9/1999 | Iglesias et al. ............. 602/16 |
| 6,306,112 B2 * | 10/2001 | Bird ....................... 602/12 |

FOREIGN PATENT DOCUMENTS

WO    PCT/US88/01712    12/1988

* cited by examiner

*Primary Examiner*—Michael A. Brown
*Assistant Examiner*—Fenn Mathew
(74) *Attorney, Agent, or Firm*—James D. Hall

(57) ABSTRACT

An orthopedic device of a therapeutic nature which includes an air bladder and an overlying gel bladder. The air and gel bladders are joined and are secured within a retainer which is adapted to be placed about a body part of a patient with the air or gel bladder being positioned next to the body part.

6 Claims, 3 Drawing Sheets

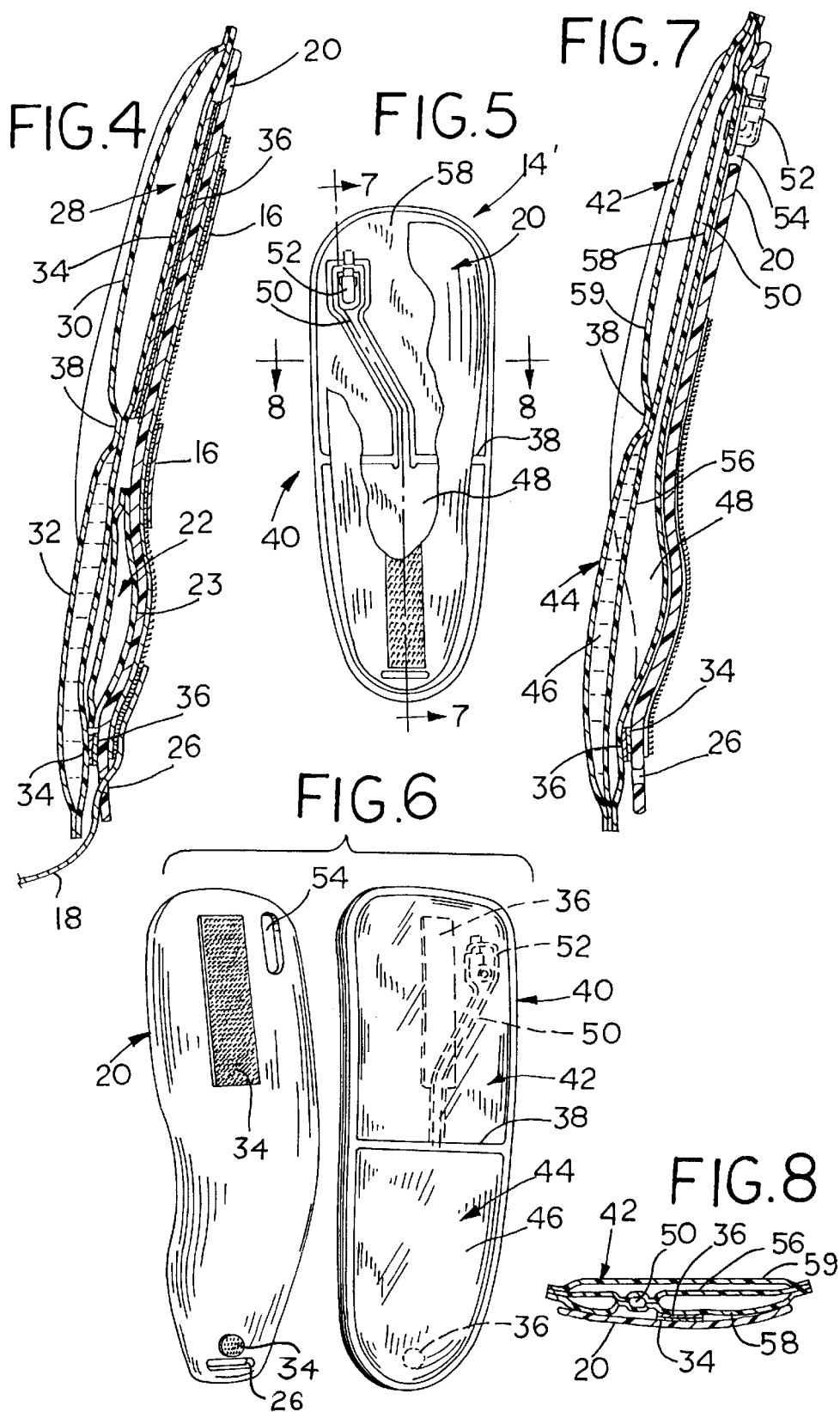

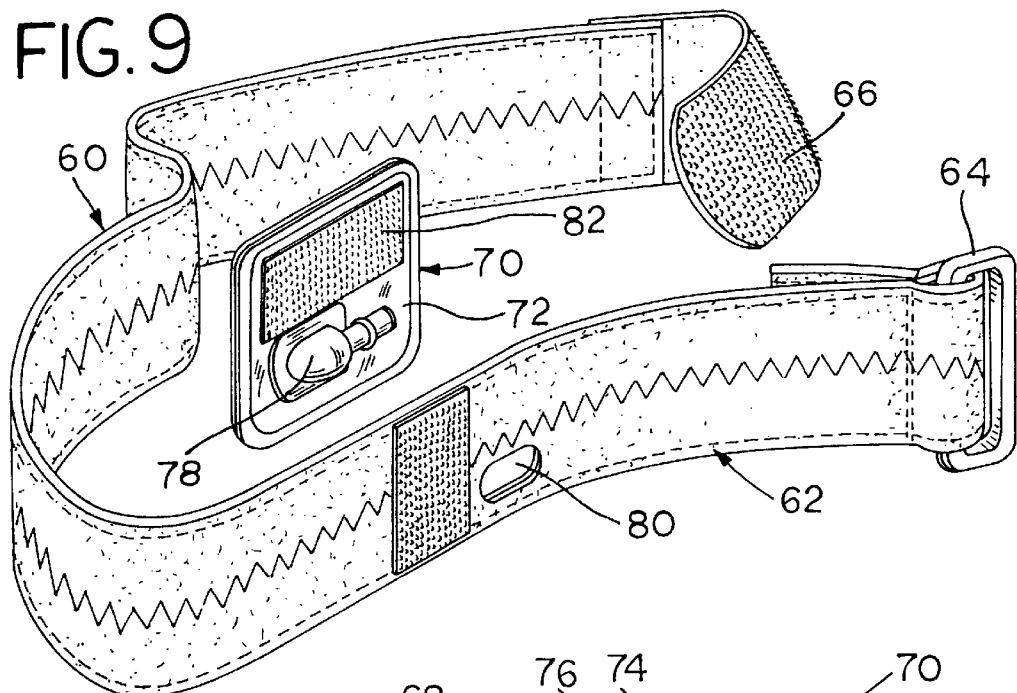
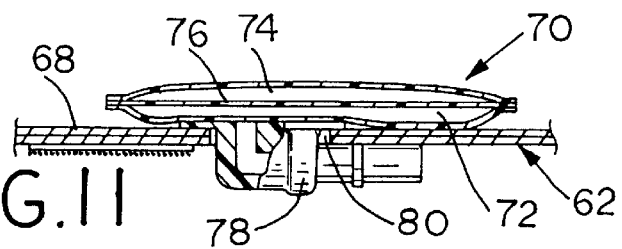
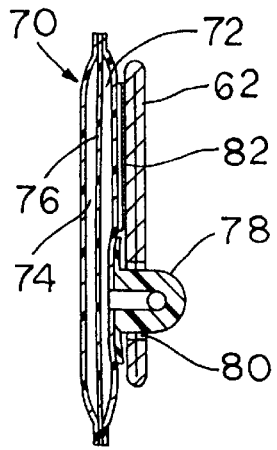
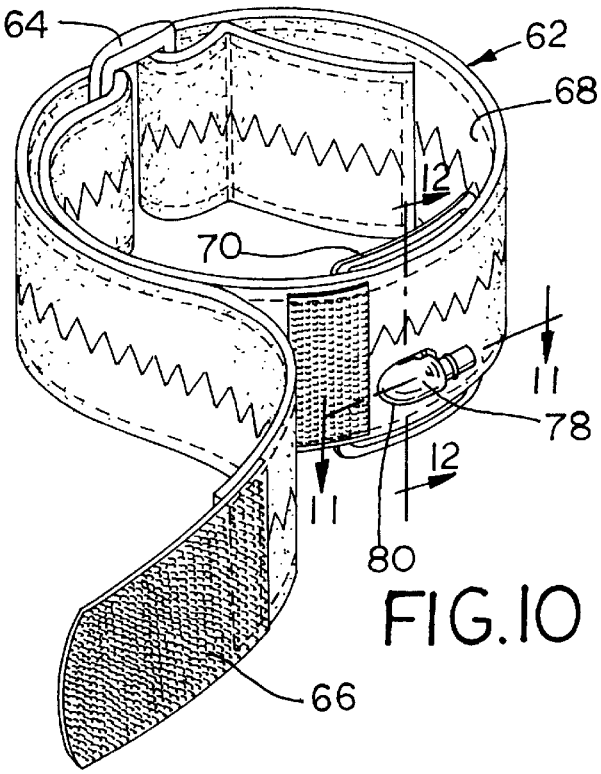

THERAPEUTIC COMBINATION GEL AND AIR BLADDER PACK

CROSS-REFERENCE TO RELATED APPLICATION

This is a continuation of provisional application Ser. No. 60/240,266, filed Oct. 13, 2000.

SUMMARY OF THE INVENTION

This invention relates to an orthopedic device and will have specific application to a therapeutic combination air and gel bladder component or pack which when used in combination with a retainer such as a splint or a wrapping can be secured about a body part of a patient with the air or gel bladder being positioned next to the body part.

In this invention there is an air bladder and a gel bladder, one overlying the other. The air and gel bladders are joined and held within a retainer such as a rigid shell member used as a leg or arm splint or a strap device used for binding about a joint with the air or gel bladder being positioned next to the body part involved.

Accordingly, it is an object of this invention to provide an orthopedic device which may be secured about a body part of a patient and which includes a combination air bladder and gel bladder joined together to form a unitary part of a device.

Another object of this invention is to provide a therapeutic device which includes a combination air and gel bladder component and which is adapted for securement to a body part of a patient.

Still another object of this invention is to provide an orthopedic device which is a splint having a cushioning air bladder used in combination with a joined gel bladder which may be heated or cooled for therapeutic purposes.

And still another object of this invention is to provide an orthopedic device which includes an air bladder and an overlying joined gel bladder adapted to be applied next to a body part of a patient with the air bladder being selectively inflatable.

Other objects of this invention will become apparent upon a reading of the following description.

BRIEF DESCRIPTION OF THE DRAWINGS

Preferred embodiments of this invention have been chosen wherein:

FIG. 4 is a longitudinal sectional view taken along the embodiment of the device shown in FIG. 3 in its assembled form.

FIG. 5 is a longitudinal side view of a second embodiment of the orthopedic device of this invention shown in assembled form and with the shell member broken away for illustrative purposes.

FIG. 6 is a perspective view of the embodiment of FIG. 5 shown with its component parts in separated or exploded form.

FIG. 7 is a longitudinal sectional view of the device of FIG. 5 as seen along line 7—7 thereof.

FIG. 8 is a cross-sectional view as seen along line 8—8 of FIG. 5.

FIG. 9 is a perspective view of another embodiment of this invention shown in the form of an elbow pad with a component parts thereof in separated or exploded form.

FIG. 10 is a perspective view of the elbow pad shown with its component parts assembled.

FIG. 11 is a fragmentary sectional view as seen along line 11—11 of FIG. 10.

FIG. 12 is a cross-sectional view as seen along line 12—12 of FIG. 10.

DESCRIPTION OF THE PREFERRED EMBODIMENTS

The preferred embodiments illustrated are not intended to be exhaustive or to limit the invention to the precise forms disclosed. They are chosen and described to best illustrate the invention and to enable one skilled in the art to utilize the invention.

Figure 1:
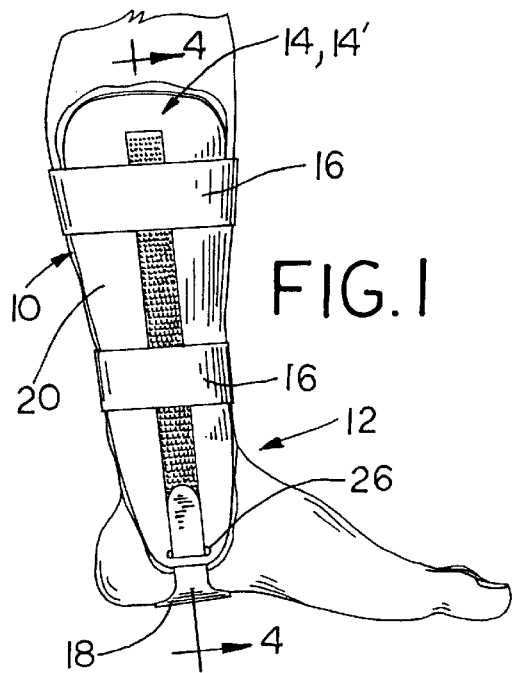
FIG. 1 is a perspective view of the orthopedic device of this invention shown in the form of a splint applied to the lower leg including the ankle of a patient and as seen from the side.
Figure 2:
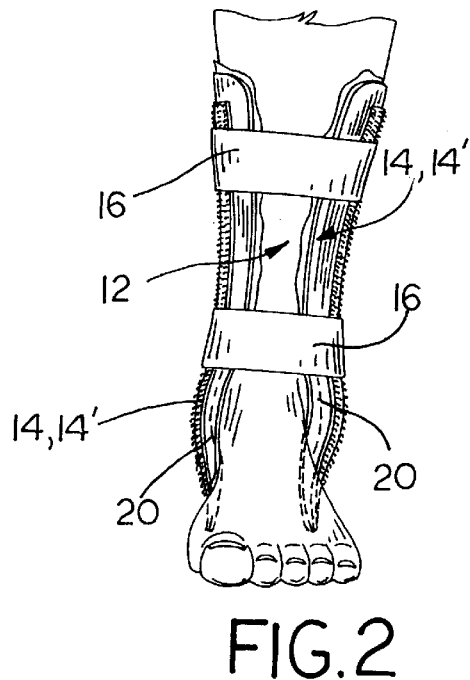
FIG. 2 is a front view of the orthopedic device of FIG. 1 as seen from the front of the leg of the patient.

The orthopedic device shown in FIGS. 1 and 2 is a splint 10 for the ankle. Splint 10 is shown applied on both sides of the lower leg 12 of a patient and includes two like constructed splint parts 14 located on opposite sides of the lower leg of foot 12 of the patient and held in position by encompassing straps or fasteners 16. Splint parts 14 are located along the sides of leg 12 by a stirrup member 18. The manner of securement of splint parts 14 by straps 16 and the use of stirrup member 18 is shown and described in prior art patents 4,628,945 and 5,007,416.

Figure 3:
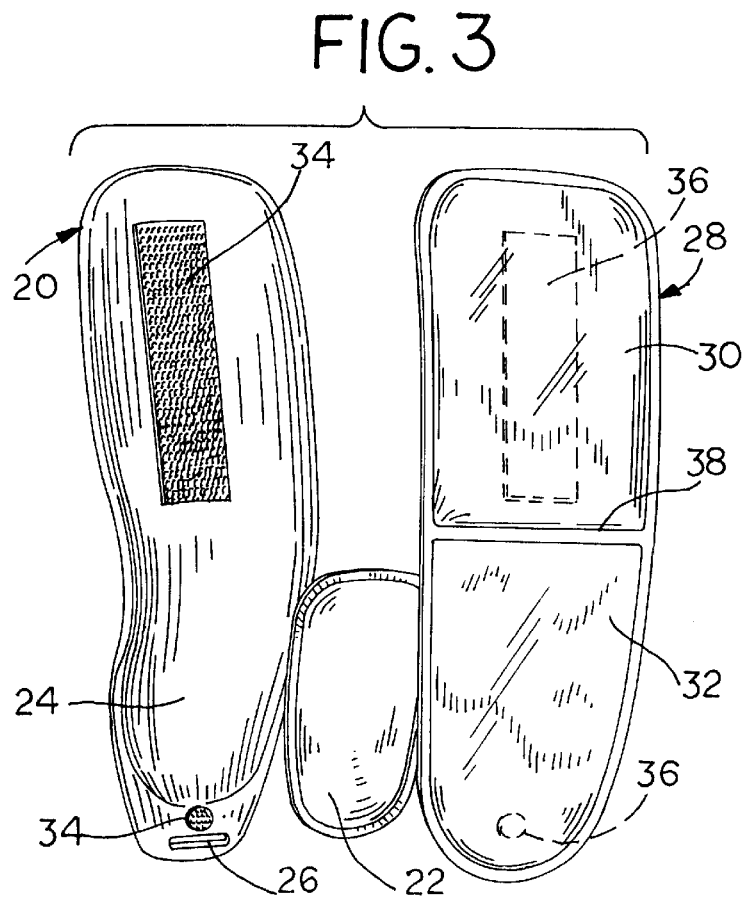
FIG. 3 is a perspective view of the component parts of one embodiment of this invention having the parts thereof in separated or exploded form for illustrative purposes.

Each splint part 14 as it forms one of the embodiments of this invention is shown in FIGS. 3 and 4 as including an outer shell member 20 which is of rigid form, generally constructed from a molded plastic material such as polyethylene. It has a shape which generally conforms to the outer configuration of lower leg 12 along its inner and outer sides. An air bladder 22 is secured, such as by an adhesive 23, in the lower portion 24 of the shell member at its interior just above the slotted opening 26 through which stirrup 18 passes when the splint part is applied to the patient. Air bladder 22 is of sealed form and as such is not inflatable by the physician or user of the splint but contains enough air to provide cushioning of the leg. Applied over the interior of shell member 20 is a cushioning member 28 which includes an upper air bladder part 30 and a lower gel bladder part 32 each forming an integral component of the cushioning member. The air bladder part 30 of cushioning member 28 is of sealed form and thus, like air bladder 22 is not inflatable by the physician or user of the splint. It contains sufficient air to provide cushioning of the splint against leg 12. Gel bladder part 32 contains a liquid gel material which has the ability to retain heat or cold and which may be manufactured in accordance with U.S. Pat. No. 3,885,403. Such gels are commonly used in the therapeutic arts for applying heat or cold to a body part of a patient. Cushioning member 28 is removably secured to shell member 20 by means of a releasable fastener such as a Velcro type fastener which includes hook material 34 secured or bonded to shell 20 and loop material 36 which is bonded to the exterior of the cushioning member. Air bladder 22 and cushioning material 28 are of an envelope construction formed of a flexible plastic material such as PVC. The air bladder part 30 and the gel bladder part 32 of the cushioning member are separated by means of a heat seal strip 38.

In FIG. 4 the splint part 14 is depicted in a vertical sectionalized form with its components in their applied positions. Air bladder 22 is permanently affixed to the inner surface of shell member 20 with cushioning member 28 applied over and extending coextensively along the shell member. The cushioning member is secured to the shell member by interlocking fastener parts 34 and 36 which allow for the removal of the cushioning member to permit it to be subjected to either heat or cooling so as to enable the gel bladder part to either retain the heat or coldness for therapeutic purposes when the cushioning member thereafter is applied to the shell member 20 and the completed splint part 14 applied about the body part of the patient. One will observe that with cushioning member 28 removably connected to the shell member 20, the gel bladder part 32 of the cushioning member overlies air bladder 22 with the gel bladder and underlying air bladder providing coordinated cushioning of the body part of the patient.

In FIGS. 5–8, a splint part $14^1$ is shown. As illustrated in the general drawings of FIG. 1 and FIG. 2, two splint parts $14^1$ are utilized to complete splint 10. Splint parts $14^1$ are of like construction with one being described in detail such as in the case of the afore-described splint part 14. Each splint part $14^1$ includes a shell member 20 over which is applied a cushioning member 40. Cushioning member 40 includes a air bladder part 42 and a gel bladder part 44. Air bladder part 42 is preferably of sealed form having sufficient air entrapped therein to provide the necessary cushioning effect of shell member 20 against the leg of the patient and is not inflatable either by the physician or the user of the splint. Gel bladder part 44 which covers the lower approximate half portion of cushioning member 40 is formed of two overlapping envelopes 46 and 48. Envelope 46 is outer most, filled with gel, and is adapted to be positioned next to the body part of the patient. As described for gel bladder part 32 relating to splint part 14, this gel is of a therapeutic liquid material with ability to retain heat or cold depending upon the therapeutic purpose and may be of the gel form found in U.S. Pat. No. 3,885,403. Underlying the gel envelope 46 of gel bladder part 44 is envelope 48 which contains air. This air envelope is preferably inflatable through a conduit 50 which extends upwardly along the back of air bladder 42 and into which is connected a valve 52 which protrudes from air bladder 42 and through an opening 54 in modified shell member 20 when the cushioning member 40 is secured to the shell member. Valve 52 includes a releasable check valve which allows the air envelope 48 to be selectively inflated with the air being retained within the envelope during usage of the splint.

Gel envelope 46 and air envelope 48 are separated by a common wall 56 which extends upwardly into the interior of air bladder part 42 to form the inner most wall of the air bladder part. This extension of wall 56 is heat sealed to the underlying wall 58 of cushioning member 40 along an upwardly longitudinally extending shape defining path to form conduit 50 which extends from valve 52 to air envelope 48. Exterior wall 59 is heat sealed along strip 38 to intermediate wall 56 to separate the air bladder part 42 from the gel bladder part 44 of the cushioning member. Wall 56 is also heat sealed along strip 38 to wall 58 except for conduit 50 (see FIG. 5) to segregate air envelope 48 from the remainder of the cushioning member. The walls of the cushioning member 40 which include walls 56 and 58 as well as the exterior wall 59 positioned inner most and against the leg of the splint user or patient are of preferably plastic material such as a medical grade PVC plastic.

Cushioning member 40 is removably secured to its receiving shell member 20 by fasteners preferably of the Velcro type which includes hook parts 34 secured to the inner surface of the shell member and loop parts 36 secured or bonded to the inner surface of the cushioning member. When cushioning member 40 is attached to shell member 20, its valve 52 is exposed through opening 54 in the shell member so as to enable air envelope 48 to be inflated either before or after the splint has been applied about the leg of the patient. Straps 16 are utilized to secure splint parts $14^1$ about the leg of the patient as previously described for the embodiment in FIG. 3 by way of fasteners with the splint parts being located and positioned through the underlying stirrup member 18 as seen in FIGS. 1 and 2.

In FIGS. 8–12, another embodiment of this invention is shown. The orthopedic device illustrated in this embodiment is an arm or leg wrap 60 having a belt part 62 which carries to a buckle 64 at one of its ends. The opposite end of belt part 62 is passed through the open buckle 64 so as to draw the belt part about the arm or leg of the patient. With the belt part snugly positioned about the arm or leg, Velcro hook fasteners 66 can be utilized to secure the free end portion of the belt part to the loop material of the belt part, thus retaining the belt part in its wrapped orientation about the arm or leg.

A removable cushioning member 70 is located at the inner surface 68 of belt part 62. Cushioning member 70 includes an air bladder part 72 and a gel bladder part 74. The bladder parts overlie one another with the gel bladder part 74 containing a therapeutic liquid gel material such as described in U.S. Pat. 3,885,403 which may be heated or cooled so as to retain heat or coldness and depending upon the therapeutic treatment desired. Gel bladder part 74 is separated from air bladder part 72 by a common wall 76 with the air bladder part being inflatable through a valve 78. Valve 78 is of a releasable check valve nature which allows air bladder part to be selectively inflated by either the physician or the user of the wrap. Cushioning member 70 is fitted against belt part inner surface 68 with the gel bladder part 74 positioned innermost so as to be locatable against the body part of the patient. Valve 78 protrudes outwardly from the air bladder part 72 through an opening 80 in belt part 62 so as to be accessible for inflating air bladder part even after the wrap has been secured about the patient. Cushioning member 70 is secured to belt part 62 by a releasable fastener 82 such as Velcro hook material which is attached to the cushioning member and which interlocks with the looped covering material of belt part 62. The cushioning member is removable to allow either heating or cooling the gel within the gel bladder part, depending upon the therapeutic requirements of the wrap.

The cushioning members afore-described and which include a gel bladder part and a inflatable air bladder part may have many applications in the orthopedic, including therapeutic fields. Particularly, such cushioning members may be used in ankle supports as well as walkers and back supports or braces.

The invention is not to be limited to the details above given but may be modified within the scope of the appended claims.

What we claim is:

1. An orthopedic device comprising a one-piece cushioning member having an upper air bladder part and a lower gel bladder part, a rigid shell member adapted to be secured about a body part, a second air bladder part positioned next to said shell member, said cushioning member positioned over said second air bladder part and extending along said shell member with said gel bladder part overlying said second air bladder part.

2. The orthopedic device of claim 1 wherein said second air bladder part forms a part of said cushioning member.

3. The orthopedic device of claim 2 wherein said cushioning member includes first, second and third overlying walls, said second wall located between said first and third walls, said first and second walls being joined to form said gel bladder part and said upper air bladder part, said second and third walls being joined to form said second air bladder part.

4. The orthopedic device of claim 3 wherein said second and third walls are joined to form an air conduit from said second air bladder part to the exterior of said third wall.

5. An orthopedic device comprising a retainer having an inner surface and an outer surface, said retainer adapted to encircle a body part, a cushioning member including an air bladder part and a juxtaposed gel bladder part, an air valve connected into said air bladder part and including a check valve part for allowing air to be introduced into said air bladder part, an opening in said retainer, means removably securing said cushioning member to said retainer at its said inner surface with said air bladder part located between said retainer and said gel bladder part and with said air valve extending through said retainer opening, said air valve being bent so as to lie against said retainer outer surface, a securement device carried by said retainer for securing the retainer about said body part with said inner surface thereof facing said body part.

6. The orthopedic device of claim 5 wherein said retainer is a strap.

* * * * *